United States Patent [19]

Dummer et al.

[11] Patent Number: 4,788,357
[45] Date of Patent: Nov. 29, 1988

[54] VINYL CHLORIDE PRODUCTION

[75] Inventors: Gerhard Dummer, Burgkirchen; Klaus Haselwarter, Burghausen; Hermann Klaus, Marktl; Ludwig Schmidhammer, Haiming; Rudolf Strasser, Burghausen, all of Fed. Rep. of Germany

[73] Assignee: Wacker-Chemie GmbH, Fed. Rep. of Germany

[21] Appl. No.: 74,137

[22] Filed: Jul. 16, 1987

Related U.S. Application Data

[63] Continuation of Ser. No. 786,811, Oct. 11, 1985, abandoned.

[30] Foreign Application Priority Data

Nov. 7, 1984 [DE] Fed. Rep. of Germany ....... 3440685

[51] Int. Cl.[4] .............................................. C07C 21/06
[52] U.S. Cl. .................................. 570/226; 570/238; 570/262
[58] Field of Search ........................ 570/226, 262, 238

[56] References Cited

U.S. PATENT DOCUMENTS 3,761,361 9/1973 Wall .
3,903,182 9/1975 Rechmeier et al. .
4,324,932 4/1982 Link et al. .

FOREIGN PATENT DOCUMENTS 1127669 7/1982 Canada .

Primary Examiner—Howard T. Mars
Attorney, Agent, or Firm—Bierman & Muserlian

[57] ABSTRACT

An improved method of producing vinyl chloride by pyrolysis of purified 1,2-dichloroethane at temperatures from 480° C. to 540° C. at a pressure of 10 to 36 bar absolute with partial utilization of the heat content of the flue gases from the pyrolysis furnace firing to preheat liquid 1,2-dichloroethane almost to its boiling temperature utilizing the flue gas waste heat to generate steam, cool the pyrolysis gas mixture in several stages and separate the hydrogen chloride from the pyrolysis gas mix in a hydrogen chloride column as well as separate vinyl chloride from the pyrolysis gas mix in a vinyl chloride monomer column.

1 Claim, 2 Drawing Sheets

VINYL CHLORIDE PRODUCTION

PRIOR APPLICATION

This application is a continuation of copending U.S. patent application Ser. No. 786,811 filed Oct. 11, 1985, now abandoned.

STATE OF THE ART

The industrial production of vinyl chloride (VCM) by pyrolysis of purified 1,2-dichloroethane (EDC) is known but the pyrolysis does not proceed quantitatively. The dichloroethane is directly heated in vapor form in a pyrolysis apparatus and cracked into vinyl chloride and hydrogen chloride (HCl) at temperatures of 480° C. to 540° C. and pressures of 10 to 36 bar absolute with conversion rates of usually 50 to 60% relative to the total throughput of gaseous 1,2-dichloroethane being maintained through appropriate temperature control in the pyrolysis apparatus. EDC can be evaporated in a separate, external evaporator by heating steam of appropriate pressure, or else, especially at pressures higher than 15 bar absolute, in the upper part of the pyrolysis apparatus by heat exchange with the flue gases from the pyrolysis furnace firing because high pressure steam necessary for the increased system pressure is usually not available in particular for reasons of economy (power generation).

Therefore, if the energy requirement for the evaporation of EDC is factored out, a heat energy of approximately 0.3 giga-Joule (GJ) is needed for each 100 kg of vinyl chloride monomer to be produced to fire a pyrolysis apparatus. Roughly 85% of this amount of heat is needed to preheat liquid EDC almost to boiling temperature, to superheat vaporous EDC to pyrolysis temperature and for the endothermal pyrolysis process, but 25% thereof are lost with the flue gases of the pyrolysis furnace firing because heat recovery is hardly economical because of the developing, relatively low flue gas temperature level of about 270° C. to 330° C.

While, pursuant to an economic necessity in present times, processes have been suggested most recently to recover a part of the heat needed to pyrolyze EDC—as long as it occurs as the heat content of the pyrolysis gases—and while the recovery of waste heat from the flue gases of a pyrolysis furnace firing system is also being practical, in some cases producing steam, such processes are not very economical because of the relatively low flue gas temperature.

OBJECTS OF THE INVENTION

It is an object of the invention to increase the flue gas temperature in combination with another measure so that the heat recovery is economically feasible and justifies the technological sophistication without thereby increasing the energy losses.

This and other objects and advantages of the invention will become obvious from the following detailed description.

THE INVENTION

In the improved process of the invention of producing vinyl chloride by pyrolysis of purified 1,2-dichloroethane at temperatures from 480° C. to 540° C. at a pressure of 10 to 36 bar absolute with partial utilization of the heat content of the flue gases from the pyrolysis furnace firing to preheat liquid 1,2-dichloroethane almost to its boiling temperature utilizing the flue gas waste heat to generate steam, cool the pyrolysis gas mixture in several stages and separate the hydrogen chloride from the pyrolysis gas mix in a hydrogen chloride column as well as separate vinyl chloride from the pyrolysis gas mix in vinyl chloride monomer column, the improvement comprises the heavy ends column for the purification of the 1,2-dichloroethane operated at a top pressure of 2 to 3.1 bar absolute is reboiled by heat exchange between the bottom and the gaseous overhead compressed to 3.2 to 6.2 bar absolute at a temperature difference from 8° to 22° C.; the sump temperature being held between 120° C. to 135° C. by appropriate bottom purge; the heat deficit resulting from the heat of vaporization reduced in accordance with the higher temperatures on the heat emission side of the heat exchanger is compensated by flashing appropriate amounts of reflux; the condensate component from the bottom heat exchanger which is returned to the column as reflux is cooled to the saturated vapor temperature corresponding to the respective top pressure by heat exchange with bottom product from the hydrogen chloride column fed to the vinyl chloride monomer column, in which process the bottom product of the hydrogen chloride column is heated accordingly or even evaporated partly; the rest of the vapor condensate collecting in the heat exchanger and representing the purified 1,2-dichloroethane is pumped uncooled at a temperature from 120° C. to 155° C. directly into the economizer of the pyrolysis apparatus; and medium pressure steam is generated from the flue gases of the pyrolysis furnace firing at a temperature level from 350° C. to 550° C. in a waste heat boiler by heat exchange with boiling water, the boiler feed water for the waste heat boiler being preheated to the boiling point in the waste heat boiler in a heat exchanger downstream of the waste heat boiler by heat exchange with the flue gases at a correspondingly lower temperature level of 60° C. to 120° C.

Purified EDC as starting material for the vinyl chloride production is obtained by distilling raw EDC from the direct and/or oxychlorination of ethylene in two successive columns for the joint separation of water and low boiler components from the high boiler components. But since the unreacted EDC from the EDC pyrolysis operation must also be freed at least of high boiler components which are formed during the pyrolysis process or have developed into high boiler components from low boiler components by reactive conversion in the pyrolysis apparatus before it can be returned to the pyrolysis apparatus, the majority of the heat energy must naturally be used to reboil the heavy ends column. Depending on the cracking depth in the pyrolysis apparatus, the mixture added to the heavy ends column is, therefore, composed of about 50 to 60% dewatered EDC free of low boiler components as bottom product of the preceding light ends column and about 40 to 50% unreacted EDC from the pyrolysis process which has been recycled. On the other hand, the light ends column often processes only raw EDC from the synthesis by direct and/or oxychlorination of ethylene.

Such distillation or rectification columns, especially those for high boiler component separation, are normally reboiled predominantly with steam at the column bottom. The lower boiling fraction is drawn off at the top, condensed and partly returned to the column again as liquid to maintain a certain reflux ratio. The other condensate fraction is removed as pure product while the bottom product is removed from the sump in which, depending on the concentration of the high boiler components and on the pressure drop across the entire column height, prevail clearly higher temperatures than at the column top. The mixture to be rectified is usually fed into the column above the column bottom.

The purification process consumes much energy, wherefore it is a further object of the invention to reduce drastically the enormous heat requirement for the separation of the high boiler components from 1,2-dichloroethane (EDC), which to date is approximately 0.25 t of steam per ton of purified EDC and approximately 0.65 t of steam per ton of vinyl chloride monomer produced, by improving the way in which the process is carried out.

These problems are solved by a method of producing vinyl chloride by thermal pyrolysis of purified 1,2-dichloroethane at temperatures from 480° C. to 540° C. at a pressure of 10 to 36 bar absolute with partial utilization of the heat content of the flue gases from the pyrolysis furnace firing apparatus to preheat liquid 1,2-dichloroethane almost to boiling temperature, utilizing the flue gas waste heat to generate steam, cool the pyrolysis gas mixture in several stages and separate the hydrogen chloride from the pyrolysis gas mix in a hydrogen chloride column as well as separate vinyl chloride from the pyrolysis gas mix in a vinyl chloride monomer column, characterized in that the heavy ends column for the purification of the 1,2-dichloroethane operated at a head pressure of 2 to 3.1 bar absolute is reboiled by heat exchange between the bottom product and the gaseous overhead compressed to 3.2 to 6.2 bar absolute at a temperature difference from 8° to 22° C.; the bottom temperature is kept between 120° C. to 135° C. by appropriate bottom purge; the heat deficit resulting from the heat of vaporization reduced in accordance with the higher temperatures on the heat emission side of the heat exchanger is compensated by flashing appropriate amounts of reflux; the condensate component from the bottom heat exchanger which is returned to the column as reflux is cooled to the saturated vapor temperature corresponding to the respective top pressure by heat exchange with bottom product from the hydrogen chloride column fed to the vinyl chloride monomer column, in which process the bottom product of the hydrogen chloride column is heated accordingly or even evaporated partly; the rest of the vapor condensate collecting in the heat exchanger and representing the purified 1,2-dichloroethane is pumped uncooled at a temperature from 125° C. to 155° C. directly into the economizer of the thermal pyrolysis appratus; and medium pressure steam is generated from the flue gases of the pyrolysis apparatus firing at a temperature level from 350° C. to 550° C. in a waste heat boiler by heat exchange with boiling water, the boiler feed water for the waste heat boiler being preheated to the boiling point in the waste heat boiler in a heat exchanger downstream of the waste heat boiler by heat exchange with the flue gases at a correspondingly lower temperature level of 60° C. to 120° C.

Surprisingly, despite an unfavorable adiabtic exponent, the top product of the heavy ends column (the gaseous overhead product) which contains EDC almost exclusively, can be compressed adiabatically to the extent this is technically possible without condensation of the gaseous overhead product. This makes it possible to use practically the entire heat of condensation of the gaseous overhead to reboil the heavy ends column. It was also surprising that the gaseous overhead consisting of the purified EDC containing impurities up to about 1 percent by weight could be compressed from its saturated vapor status without problem to at least 15 bar without the mentioned difficulties of a possible premature condensation occuring. Also, there are surprisingly no difficulties caused by the possibility that the impurities or the EDC itself could decompose during compression, e.g. forming corrosive substances or polymer like or tarry crack products.

Such resin deposits could cause rotor tarnishing problems in screw-type compressors or attrition problems in turbo-compressors by imbalance or quite generally shaft sealing problems. As is known, especially on hot metal surfaces, 1,2-dichloroethane can experience a thermal polycondensation, catalyzed by hydrogen chloride in which more hydrogen chloride is split off and tarry polymers are formed. In addition, the so called purified EDC also contains, besides hydrogen chloride (HCl), other chlorohydrocarbons which are partly desirable as promotors of the thermal pyrolysis of EDC and are partly permitted within certain limits for economy reasons because, as experience teaches, they have no harmful influence on the pyrolysis process. Such contaminations contained in the purified EDC in the range from 0.01 to 0.15 percent by weight each are e.g. carbon tetrachloride, chloroform, 1,1-dichloroethane, 1,1,2-trichloroethane trichloroethylene and isomeric dichloroethylene. Since these compounds mentioned are in part far less thermally stable than 1,2-dichloroethane, one could assume that the great majority of these impurities are decomposed during compression thereby forming resin products. In addition, the formation of extremely corrosive decomposition products from some of these impurities was to be expected.

It is known, for instance, that carbon tetrachloride readily splits into chloro and trichloromethyl radicals which are highly corrosive which then can cause severe compressor damage. It was also expected that, through possible decomposition reactions, the 1,2-dichloroethane, for instance, could change so decisively in its composition that in the subsequent pyrolysis process difficulties regarding the purity of the vinyl chloride produced and the kinetics of the pyrolysis process could arise under these circumstances.

The thermocompression (compression of the gaseous overhead) is the more economical, the lower the compression ratio of gaseous overhead product under the aspect of a sufficient temperature difference between the compressed gaseous overhead product and the bottom temperature of the column can be kept. A temperature difference of 8° to 22° C. suffices to have available enough driving force for the heat exchange between the compressed gaseous overhead and the bottom product of the heavy ends column at economically feasible heat exchanger surfaces.

On the other hand, the top pressure of the column cannot be raised arbitrarily because this would greatly increase the bottom temperature in accordance with the higher bottom pressure which is composed of the top pressure and the pressure drop across the entire column height so that the bottom temperature would also increase. This can cause a faster fouling (quicker deposition of sludge as far as even to plugging) of the heat exchanger on the bottom product side. Practice has shown that a bottom temperature between 120° C. to 135° C. is advantageous regarding the fouling of the heat exchanger. At 0.5 bar pressure drop across the column and while maintaining the necessary temperature difference between gaseous overhead and bottom product, it is desired to bring the gaseous overhead to a temperature level of 128° C. to 157° C. max. by adiabatic compression. This means column top pressures of 2 bar absolute to 3.1 bar absolute max., and gaseous overhead product pressures after compression of 3.2 bar absolute to 6.2 bar absolute max, respectively. Accordingly, the compression ratio is preferably between 1.6 and 2.0.

To improve the heat exchange, the small amounts of adiabatic superheat is preferably removed by injecting appropriate amounts of liquid 1,2-dichloroethane into the compressed gaseous overhead product before it enters the heat exchanger for column reboiling. The small heat deficit resulting from the different heats of evaporation and condensation on the heat emitting of gaseous overhead product side and on the heat absorbing column bottom side of the heat exchanger, respectively due to the specific heats of evaporation or condensation dropping with rising temperatures, can preferably be compensated by flashing an appropriate amount of liquid reflux. Since the reflux must be brought to the saturated vapor temperature of the gaseous overhead on the suction side of the compressor, which is accomplished by appropriate cooling with water or, preferably, by heat exchange with bottom product from the hydrogen chloride column, utilizing the heat content of the reflux resulting from the temperature difference of the gaseous overhead product before and after compression, it is also possible to cool the reflux only to the point where the required amount of vapors develops upon flashing the entire amount of reflux and where the saturated vapor temperature corresponding to the column top pressure is reached. Consequently, the condensed gaseous overhead collecting in the bottom heat exchanger has a temperature of about 125° C. to 155° C.

If this condensate or purified 1,2-dichloroethane is pumped without intermediate cooling directly into the economizer of the pyrolysis apparatus, the flue gas temperature of the pyrolysis furnace firing will rise to 370° C. to 580° C. at the economizer outlet. This is a temperature level at which heat recovery with steam generation is extremely economical.

Referring to the drawings.

Figure 1:
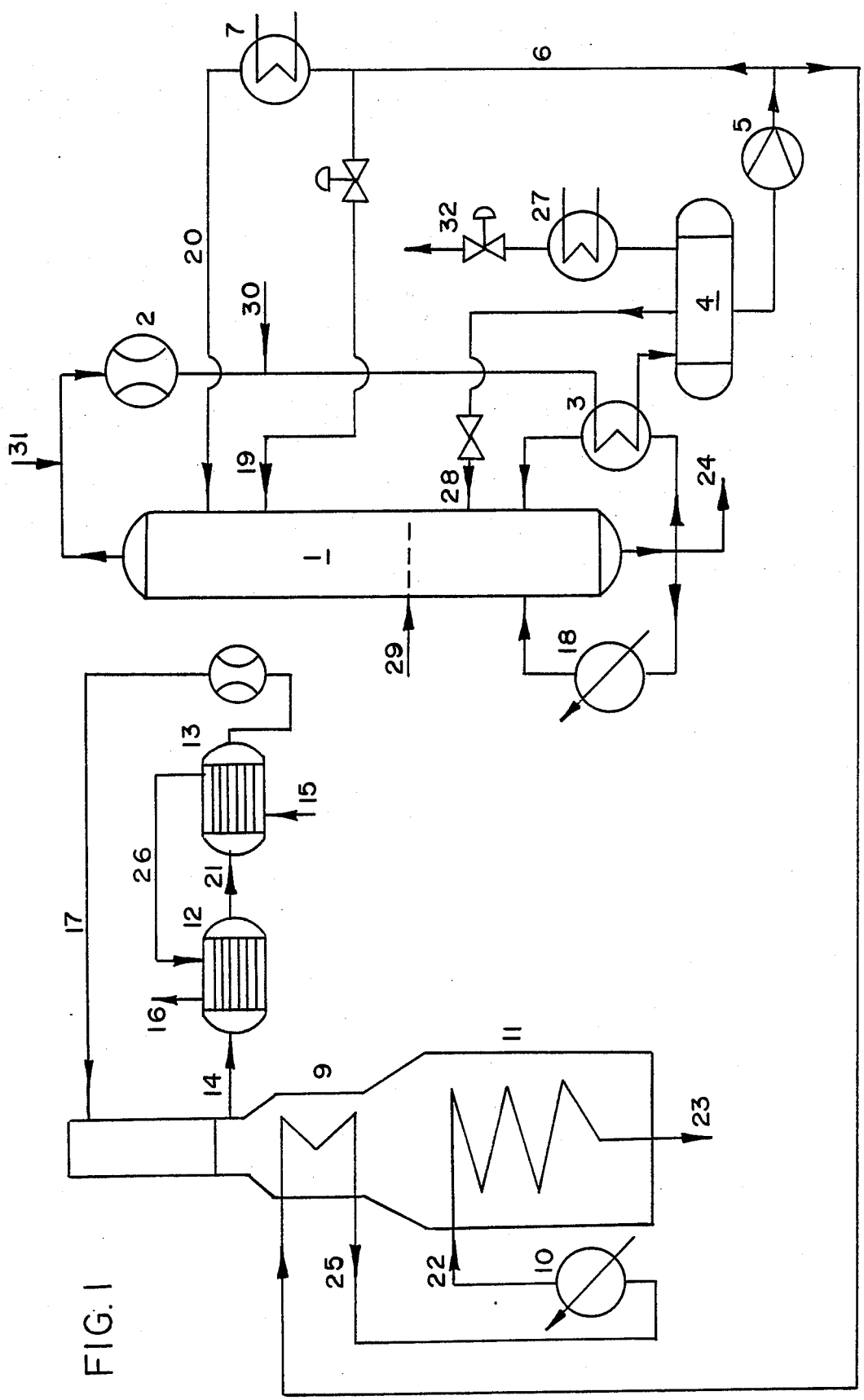
FIG. 1 illustrates one advantageous embodiment of equipment for the execution of the method of the invention.

The raw EDC to be purified is fed into the heavy ends column of FIG. 1 at 29 and its lower end which is the bottom or column sump, the column has at least one draining device offering the possibility, of draining the high boiler component fraction through pipeline 24 which can be blocked, while being connected by pipes to the bottom heat exchanger 3 and possibly to a supplemental reboiler 18. Other pipes connect the heat exchanger and possibly the supplemental reboiler for returning of the heated bottom content into the lower section of the column. The column top is connected via a line to a compressor 2 such as a turbo-compressor and for pressure maintenance, an inert gas like nitrogen can be fed in through inlet 31.

A pipe connects the pressure side of compressor 2 to the bottom heat exchanger 3 and also to collecting vessel 4 for the purified condensed EDC. At 30, EDC from vessel 4, for instance, can be fed additionally into the connecting line from compressor 2 to heat exchanger 3, e.g. to regulate or control the temperature of the EDC serving in 3 as heating medium. The possibly present supplemental reboiler 18 and the block valve-equipped line from vessel 4 to feeding point 28 serve in the usual manner only to get the installation started until a nearly stationary state is attained. Gaseous materials which cannot be condensed at the usual operating temperature can be expelled via condenser 27, e.g. a water cooler, and control valve 32. The condensed EDC fraction is removed from the vessel 4 by pump 5.

A part of the EDC fraction is returned to the rectifying section of column 1, through pipe 6 and heat exchanger 7 as well as pipe 20. In addition, for the control of disorders or for the supply of additional heat there is the possibility to feed into the rectifying section at 19 more superheated liquid EDC through a pipe which can either be blocked or whose flow rate can be controlled. Finally, the EDC can be introduced through pipe 8 directly into economizer 9 of pyrolysis apparatus 11 and from there through evaporator 10 into pyrolysis apparatus 11 at 22. The reaction mixture is removed from apparatus 11 at 23 and conveyed for further processing (not shown).

Flue gas line 14 conducts the flue gases via waste heat boiler 12 and heat exchanger 13 to a blower which blows the flue gases into the atmosphere through a pipe 17. At 15, water is introduced into heat exchanger 13 and heated, then conducted through pipe 26 into waste heat boiler 12 from which the generated steam can be conducted away at 16.

The method of the invention saves roughly 0.65 t of steam per ton of vinyl chloride produced. The electrical energy required for the thermo compression of the gaseous overhead product amounts to about 31 kWh/t of vinyl chloride produced, i.e. only about 9% relative to the steam savings from a purely caloric view-point. In addition, about 0.15 t of steam (of 16 bar) is generated per ton of vinyl chloride produced which steam can be used elsewhere. This results according to the invention in an extremely economical vinyl chloride production because the vinyl chloride production cost is burdened with roughly 0.80 t less steam per ton of vinyl chloride due to the energy savings in the high boiler separation of 1,2-dichloroethane as starting material for the vinyl chloride production and in the vinyl chloride monomer column through heat exchange between reflux and bottom product from the hydrogen chloride column and through steam generation from the recovery of flue gas heat. Despite higher bottom temperatures in the heavy ends column, the life time of the bottom heat exchanger for reboiling the heavy ends column by compressed gaseous overhead product is roughly one year.

According to another embodiment, supplemental reboiler 18 can continue to be also in almost stationary to stationary operation if one wants to do without the flash evaporation by the return of purified EDC.

While it is also imaginable, especially at high compression (e.g. up to 15 bar) in turbo-compressor 2 to feed the purified EDC coming from the compressor directly into pyrolysis apparatus 11 at 22, this embodiment represents an extremely rigid connection between EDC purification and EDC pyrolysis so that, in the event of trouble either in the purification or in the pyrolysis, it is always the entire installation which suffers and may have to be shut down. In contrast thereto, the method of the invention offers the possibility, also in the event of such disorders, to keep the unaffected part of the installation running virtually unhindered by adding, for instance, an EDC storage tank. This makes it possible either to buffer the freshly purified EDC or, in the event of EDC purification trouble, the pyrolysis apparatus can be further supplied from such an EDC storage tank.

In the following examples there are described several preferred embodiments to illustrate the invention. However, it is to be understood that the invention is not intended to be limited to the specific embodiments. All pressures are absolute pressures and ppm means mg of substance per kg of total weight of EDC fraction.

EXAMPLE 1

Figure 2:
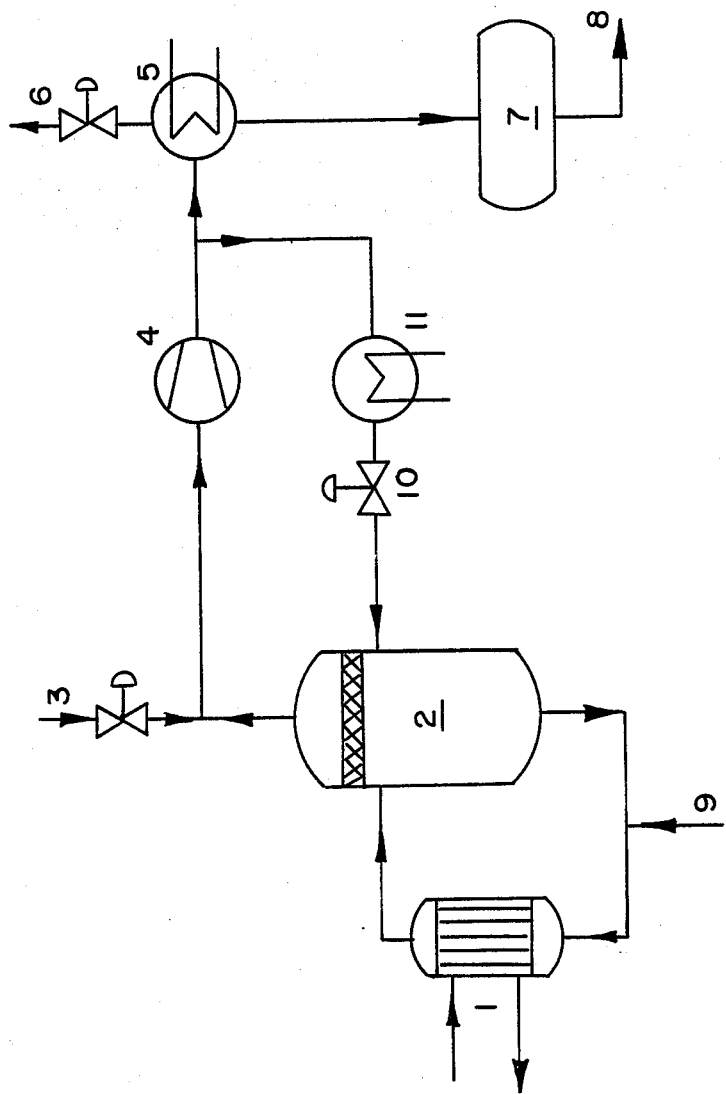
FIG. 2 illustrates a test equipment reboiling the heavy ends column by heat exchange and for investigating the influence of gaseous overhead product compression upon the EDC composition.

1,2-dichloroethane used in the present example was comprised of 99.4% by weight of dichloroethane, 10 weight ppm of vinyl chloride, 80 weight ppm of cis-1,2-dichloroethylene, 60 weight ppm of trans-1,2-dichloroethylene, 360 weight ppm of 1,1-dichloroethane, 250 weight ppm of chloroform, 1250 weight ppm of carbon tetrachloride, 500 weight ppm of trichloroethylene, 300 weight ppm of 1,1,2-trichloroethane, 3000 weight ppm of benzol and 150 weight ppm of hydrogen chloride and the apparatus used was that of FIG. 2.

8.32 t/h of the 1,2-dichloroethane were evaporated in a steam-heated, tube bundle reboiler 1 at 1.42 bar pressure and the associated saturated vapor temperature was 96° C. The 1,2-dichloroethane to be evaporated was supplied through line 9 in a constant flow and after separating the liquid vapor mixture coming out of the reboiler 1 in a separator 2 equipped with a demister, the evaporated liquid was aspirated by a single-stage screw type compressor 4. To keep the suction pressure constant during the starting phase or to maintain the destinated pressure, nitrogen heated to 97° C. was added at 3. The evaporated liquid was compressed in compressor 4 to 5.05 bar pressure, the pressure being kept constant by back pressure control valve 6. After compression, the evaporated liquid reached a temperature of 158° C. and the compressed 1,2-dichloroethane vapor was condensed in water-cooled condenser 5, the condensate running down was collected in a basin 7. Non-condensable components (mostly nitrogen) were separated, and the condensate was then removed through line 8 for further processing elsewhere. The uncondensable components were removed through back pressure control valve 6. A by-pass line with control valve 10 and cooler 11 was available for starting and for controlling screw-type compressor 4. After the severe treatment in vapor form, carried out by adiabatic compression with superheating by about 10 degrees over the saturated vapor temperature corresponding to the destinated pressure, the condensed 1,2-dichloroethane removed at 8 had the following composition: 99.4 weight % of 1,2-dichloroethane and 8 weight ppm of vinyl chloride, 75 weight ppm of cis-1,2-dichloroethylene, 50 weight ppm of trans-1,2-dichloroethylene, 361 weight ppm of 1,1-dichloroethane, 249 weight ppm of chloroform, 1252 weight ppm of carbon tetrachloride, 500 weight ppm of trichloroethylene, 302 weight ppm of 1,1,2-trichloroethane, 2998 weight ppm of benzol and 40 weight ppm of hydrogen chloride.

Except for a minor decrease of the lower boiling components of the original 1,2-dichloroethane which were partly removed with the nitrogen in back pressure control valve 6 such as hydrogen chloride, vinyl chloride, trans-1,2-dichloroethylene and cis-1,2-dichloroethylene, no difference was detectable when comparing the analyses before and after the compression. After three weeks of experimental operation, no deposits and contaminations were detectable in the compressor. The composition of the 1,2-dichloroethane after the compression and condensation of the evaporated liquid remained always the same. In the further processing of the 1,2-dichloroethane removed at 8, no differences from uncompressed 1,2-dichloroethane of the same composition were found in vinyl chloride direction.

EXAMPLE 2

Using the procedure of Example 1, the same evaporated liquid was compressed to 15 bar in a two-stage compressor whereby the compressed evaporated liquid heated up to 238° C. After one week of continuous experimental operation as described in Example 1, no differences in the composition of the 1,2-dichloroethane before and after compression were found nor were deposits or contamination of the compressor observed.

EXAMPLE 3

The procedure was analogous to Example 1, except that the condensed 1,2-dichloroethane obtained at 8 was returned to evaporator 1 at 9. Despite the recirculation of the 1,2-dichloroethane, its composition did not change after a total of 14 days of experimental operation, except for low boiling contaminations which were automatically expelled at 6 with the nitrogen. The circulating 1,2-dichloroethane was compressed approximately 670 times.

EXAMPLE 4

The procedure was analogous to Example 1 but, the compressed evaporated liquid was used for the evaporation of 1,2-dichloroethane by by-passing water cooler 11 and introducing the compressed evaporated liquid instead of the heating steam into reboiler 1, the evaporation taking place due to heat exchange between the condensing evaporated liquid and the 1,2-dichloroethane entering at 9 as rerun. The condensed evaporated liquid draining from the reboiler was removed through 5,7 and 8. A portion of the condensed evaporated liquid was flushed to the pressure on the suction side of the compressor and fed to the suction side of compressor 4 at the rate of about 1 t/h to cover the heat losses or compensate the differences in the heat evaporation at the different pressures and temperatures while uncondensed nitrogen escaped at 6. The 1,2-dichloroethane composition before and after compression remained approximately the same and the test lasted two days.

EXAMPLE 5

The apparatus of FIG. 1 was used in this Example and heavy ends column 1 was charged at 29 with 74.5 t/h of raw 1,2-dichloroethane of the following composition: 99.08 weight % of 1,2-dichloroethane and 10 weight ppm of vinyl chloride, 80 weight ppm of cis-1,2-dichloroethylene, 60 weight ppm of trans-1,2-dichloroethylene 360 weight ppm of 1,1-dichloroethane, 250 weight ppm of chloroform, 1250 weight ppm of carbon tetrachloride, 480 weight ppm of trichloroethylene, 3100 weight ppm of 1,1,2-trichloroethane, 2980 weight ppm of benzol, 160 weight ppm of hydrogen chloride and 350 weight ppm of other high boilers.

Under equilibrium of the column, the temperature adjusted to 127° C. in the bottom of the heavy ends column at a pressure of 3 bar due to the continuous removal of 1.5 t/h of bottom product at 24. At the top of the column, 136.4 t/h of gaseous overhead product of a saturated vapor temperature of 118° C. were aspirated by turbo-compressor 2 at 2.5 bar pressure and compressed to 4.5 bar. In this process, the gaseous overhead gas heated to 145° C., i.e. superheated by about 3° C. 886 kWh of electrical energy were consumed for the compression of the gaseous overhead. About 1.7 t/h of liquid condensate with a temperature of about 142° C. from collector 4 were injected at 30 to remove the superheat from the gaseous overhead, thereby improving the heat transfer in heat exchanger 3. The now saturated, gaseous overhead product vapor reached heat exchanger 3 at a temperature of 142° C. and heat exchanger 3 was designated as tube bundle reboiler with bottom product in the tubes, the compressor gasous overhead condensing due to heat exchange with 127° C. bottom product on the shell side of the heat exchanger while the circulating bottom product evaporated in the tubes due to the liberated heat of condensation heat, thereby reboiling the column. The condensed gaseous overhead product was drained from heat exchanger 3 into collector 4.

The compression pressure was kept at 4.5 bar at 32, by back pressure control valve. Uncondensable components of the compressed gaseous overhead were removed through control valve 32 after cooling in water cooler 27, especially small amounts of nitrogen which had been added at 31 to maintain the desired destinated pressure. Gaseous overhead condensate was returned to the column as reflux of about 140° C. by pump 5. To compensate for the heat deficit at heat exchanger 3 which is a result of the specific heat condensation of 1,2-dichloroethane being lower by roughly 8.5 kJ/kg at 142° C. than the specific heat of evaporation of 1,2-dichloroethane at 127° C. and to cover heat losses, sufficient reflux from line 6 was flashed into the column through line 19 that approx. 4 t/h of flash vapors were obtained. The rest of the approx. 140° C. reflux was cooled by 81° C. bottom product from the hydrogen chloride column which, released from 9.8 bar to about 6.5 bar, flowed to the succeeding vinyl chloride monomer column, down to 118° C. before entering the column through line 20 while roughly 16% of the bottom product of the hydrogen chloride column evaporated. By this way, only 6.4 t/h of 20 bar steam were needed to reboil the vinyl chloride monomer column.

73 t/h of purified of 1,2-dichloroethane at a temperature of about 140° C. were pumped through line 8 into the economizer of pyrolysis apparatus 9 and the composition of the purified 1,2-dichloroethane was as follows: 99.4 weight % of 1,2-dichloroethane and 11 weight ppm of vinyl chloride, 78 weight ppm of cis-1,2-dichloroethylene, 61 weight ppm of trans-1,2-dichloroethylene 359 weight ppm of 1,1-dichloroethane, 250 weight ppm of chloroform, 1250 weight ppm of carbon tetrachloride, 481 weight ppm of trichloroethylene, 298 weight ppm of 1,1,2-trichloroethane, 2981 weight ppm of benzol and 158 weight ppm of hydrogen chloride.

The liquid 1,2-dichloroethane pumped by a pressure of 17 bar was preheated to 190° C. in economizer 9 through heat exchange with the flue gases of the pyrolysis apparatus. It subsequently reached steam-heated evaporator 10 via line 25 where it was evaporated at 22 at a pressure of 13 bar into the pyrolysis furnace corresponding to a boiling temperature of about 195° C. In the radiation section of pyrolysis apparatus 11, vaporous 1,2-dichloroethane was first heated to pyrolysis temperature and then pyrolyzed at an outlet temperature of about 507° C. into vinyl chloride and hydrogen chloride at 61.2% conversion. The pyrolysis gas mixture, essentially consisting of 28 t/h of vinyl chloride, 16.4 t/h of hydrogen chloride and 28.3 t/h of unconverted 1,2-dichloroethane, left the pyrolysis apparatus at 23, was then cooled by known methods and reached, partly gaseous and partly liquid, the hydrogen chloride column where 16.4 t/h of hydrogen chloride were removed through the top. The bottom product of the hydrogen chloride column consisting of 28 t/h of vinyl chloride and 23.8 t/h of unconverted 1,2-dichloroethane was separated, after heating and partial evaporation in heat exchanger 7, in the succeeding vinyl chloride column where 28 t/h of pure vinyl chloride were obtained at the top while 28.3 t/h of unconverted 1,2-dichloroethane were removed through the bottom drain and recycled for purification and re-use.

The flue gasees from the pyrolysis apparatus which were developed by 2200 m$^3$/h of natural gas and 25300 m$^3$/h of air heated to about 100° C. left economizer 9 at a temperature of about 415° C. and entered waste heat boiler 12 at 14. There, 4.1 t/h of water at almost boiling temperature entering waste heat boiler through line 26 were evaporated. The 4.1 t/h of 16 bar steam generated entered the steam network at 16 and at the outlet of the waste heat boiler 12, the flue gas temperature was about 210° C. The flue gases flowed through line 21 into boiler feed water preheater 13 where 4.1 t/h of 80° C. boiler feed water entering the preheater at 15 bar were preheated to about 203° C. before entering waste heat boiler 12 through line 26. The flue gases cooled further in preheater 13 and were discharged into the atmosphere through line 17 by a suction blower at a temperature of about 146° C. The service life of heat exchanger 3 was one year.

The high boiler column was started up with the aid of starting reboiler 18 operated with heating steam, or else with nitrogen which is added at 31 on the suction side of gaseous overhead compressor 2, and heats up much more than EDC due to its adiabatic exponent and is circulated through line 28 as long as the correct gaseous overhead temperature is reached at the top of column 1.

COMPARATIVE TEST

The procedure was analogous to Example 5, but without thermo-compression (gaseous overhead compression). Roughly 18.5 t/h of 16 bar steam were needed at boiler 18 to heat heavy ends component column 1 and the purified 1,2-dichloroethane of the same composition as in Example 5 reached economizer 9 at about 116° C. Preheating, evaporation, pyrolysis and processing of the pyrolysis gas mixture were carried out as described in Example 5 and 7 t/h of 20 bar steam were required to heat the vinyl chloride monomer column. The temperature of the flue gas leaving economizer 9 was about 315° C. Through heat exchange in waste heat boiler 12 and boiler feed water preheater 13, the flue gas cooled down to roughly 177° C. before discharge into the atmosphere. About 2 t/h of 16 bar steam were generated in the waste heat boiler.

Compared to the method of the invention, the production of vinyl chloride used to be considerably less economical because the steam requirement per ton of vinyl chloride produced was roughly 0.77 t higher.

Compared thereto, the additional electric power consumption in the method of the invention for the thermocompression is not significant. Moreover, a not inconsiderable contribution to environmental protection was achieved by the method of the invention because the waste gases enter the atmosphere at a considerably lower temperature.

Various modifications of the process of the invention may be made without departing from the spirit or scope thereof and it should be understood that the invention is intended to be limited only as defined in the appended claims.

What we claim is:

1. In a method of producing vinyl chloride by pyrolysis of purified 1,2-dichloroethane at temperatures from 480° C. to 540° C. at a pressure of 10 to 36 bar absolute with partial utilization of the heat content of the flue gases from the pyrolysis furnace firing to preheat liquid 1,2-dichloroethane almost to its boiling temperature utilizing the flue gas waste heat to generate steam, cool the pyrolysis gas mixture in several stages and separate the hydrogen chloride from the pyrolysis gas mix in a hydrogen chloride column as well as separate vinyl chloride from the pyrolysis gas mix in a vinyl chloride monomer column, the improvement comprising the heavy ends column for the purification of the 1,2-dichloroethane operated at a top pressure of 2 to 3.1 bar absolute is reboiled by heat exchange between the bottom and the gaseous overhead compressed to 3.2 to 6.2 bar absolute at a temperature difference from 8° to 22° C.; the bottom temperature being held between 120° C. and 135° C. by appropriate bottom purge; the heat deficit resulting from the heat of vaporization reduced in accordance with the higher temperature on the heat emission side of the heat exchanger is compensated by flashing appropriate amounts of reflux; the condensate component from the bottom heat exchanger which is returned to the column as reflux is cooled to the saturated vapor temperature corresponding to the respective top pressure by heat exchange with bottom product from the hydrogen chloride column fed to the vinyl chloride monomer column, the rest of the vapor condensate collected in the vapor phase condensate vessel and representing the purified 1,2-dichloroethane is pumped uncooled at a temperature from 125° C. to 155° C. directly into the economizer of the pyrolysis apparatus; and medium pressure steam is generated from the flue gases of the pyrolysis furnace firing at a temperature level from 350° C. to 550° C. in a waste heat boiler by heat exchange with boiling water, the boiler feed water for the waste heat boiler at a correspondingly lower temperature level of 60° C. to 120° C. being preheated to the boiling point in the waste heat boiler in a heat exchanger downstream of the waste heat boiler by heat exchange with the flue gases.

* * * * *